United States Patent [19]

Chetcuti

[11] Patent Number: 5,436,353
[45] Date of Patent: Jul. 25, 1995

[54] DITHIOPENTACENE DERIVATIVES, THEIR PREPARATION AND THE USE THEREOF AS ELECTRON ACCEPTORS ON CHARGE TRANSFER COMPLEXES

[75] Inventor: Peter Chetcuti, Basel, Switzerland

[73] Assignee: Ciba-Geigy Corporation, Ardsley, N.Y.

[21] Appl. No.: 106,100

[22] Filed: Aug. 12, 1993

[30] Foreign Application Priority Data

Aug. 20, 1992 [CH] Switzerland ............. 2591/92

[51] Int. Cl.$^6$ ............. C07D 339/00; C07D 339/08; H01B 1/00
[52] U.S. Cl. ............. 549/15; 252/500
[58] Field of Search ............. 564/105, 248; 252/500; 549/15

[56] References Cited

U.S. PATENT DOCUMENTS

| | | | |
|---|---|---|---|
| 4,900,842 | 2/1990 | Robin et al. | 549/36 |
| 5,009,812 | 4/1991 | Finter et al. | 252/500 |

FOREIGN PATENT DOCUMENTS

| | | |
|---|---|---|
| 281449 | 9/1988 | European Pat. Off. |
| 454874 | 11/1991 | European Pat. Off. |

OTHER PUBLICATIONS

J. Chem. Research S (1991) Martinez et al. pp. 246 & 247 No Month Available.
Rer, Deutsch, Chem. Ges., Brass et al., 55: 2543–2568 (1992) No Month Available.
Synthetic Metals, Rak et al, 41–43 (1991) pp. 2365–2375 No Month Available.
Chem. Mater, vol. 2, No. 4 (1990) pp. 339–340 No Month Available.
J. Amer. Chem. Soc. vol. 102, No. 17 Jaeger et al, pp. 5435–5442 (1980), Aug.
Can J. Chem. 43; 1448–1453 (1965) Sandin et al, Nov.
Canadian Journal of Chemistry, L. R. Melby vol. 43, No. 5, May 1965 pp. 1448–1453, May 1965.
J. Am Chem. Soc. vol. 102, C. D. Jaeger et al. No. 17 Aug. 1980 pp. 5435–5442.
S. F. Rak et al, Synthetics Metals 41–43 (1991) pp. 2365–2375 No Month Available.
S. Miller et al, Chem. Materials vol. 2, 1990 pp. 339–340 No Month Available.
E. S. Martinez et al. J. Of Chem. Res. (5) (1991) pp. 246–247.
E. Ahsbahs et al. J. of Chem. Res. (5) 1992 pp. 184–185 No Month Available.

*Primary Examiner*—Paul Lieberman
*Assistant Examiner*—M. Kopec
*Attorney, Agent, or Firm*—George R. Dohmann

[57] ABSTRACT

The present invention relates to novel dithiopentacene derivatives, to a process for their preparation, to charge transfer complexes obtained from said dithiopentacene derivatives as electron acceptors and unsubstituted or substituted ferrocene, chalcogenated fulvalenes or aromatic nitrogen compounds as electron donors. The invention further relates to a process for their preparation; to compositions comprising a plastics material and such a CT complex; and to the use of said CT complexes as electrical conductors, conveniently for the production of electrically conductive films, foils or coatings.

13 Claims, No Drawings

DITHIOPENTACENE DERIVATIVES, THEIR PREPARATION AND THE USE THEREOF AS ELECTRON ACCEPTORS ON CHARGE TRANSFER COMPLEXES

The present invention relates to novel dithiopentacene derivatives; to a process for their preparation, to charge transfer complexes (hereinafter abbreviated to CT complexes) obtained from said dithiopentacene derivatives as electron acceptors; and to unsubstituted or substituted ferrocene, chalcogenated fulvalenes or aromatic nitrogen compounds as electron donors. The invention further relates to a process for their preparation; to compositions comprising a plastics material and such a CT complex; and to the use of said CT complexes as electrical conductors, conveniently for the production of electrically conductive films, foils or coatings.

The compound dinaphtho[2,3-b;2',3'-e][1,4]dithiine-5,7,12,14-tetraone (abbreviated to DNDT) is described by E. S. Martinez et al. in J. Chem. Research (S), pp.246-247. (1991). At room temperature, DNDT has a very low conductivity of 10$^{-11}$ S/cm as pressed pellet. Further, a process for the preparation of this compound is described by K. Brass and L. Köhler in Ber. Deutsch. Chem. Ges., 55, pp. 2543-2568 (1992). Dinaphtho[2,3-b;2',3'-e][1,4]dithiinones and -cyanoimines have not been described.

Powdered CT complexes comprising tetra-substituted pentacenecyanoimine and tetrathiofulvalene as electron donors, and single crystals of tetra-substituted pentacenecyanoimine and alkali metal cations and tetraalkylammonium are described in Synthetic Metals, 41-43, pages 2365-2375 (1991). However, powdered materials are insufficiently able to enhance the conductivity of polymer materials as, after processing, the particles are encapsulated by the polymer material and therefore insulated.

In addition, L. Miller et al. describe 5,7,12,14-pentacenetetracyanoimine in Chem. Mater. 2, pp. 339-40 (1990) as electron acceptor for the preparation of radical cation salts with alkali metals such as sodium and potassium.

U.S. Pat. No. 5,009,812 discloses antistatically treated and electrically conductive polymers that contain e.g. CT complexes of tetrathio-, tetraseleno- or tetratellurotetracenes as electron donors and halogens or oxygen as electron acceptors. In these materials the CT complexes form needle networks in the polymer matrix.

CT complexes of tetracyanoquinodimethane (TCNQ) as electron acceptors and N-aromatic compounds as donors are desribed, inter alia, by C. D. Jaeger and A. J. Bard in J. Am. Chem. Soc., Vol. 102, No. 17, pp. 5435-5442 (1980), and by L. Russell Melby in Can. J. Chem., Vol. 43, pp. 1448-1453 (1965). These CT complexes do not always crystallise in needle form and, because of their crystalline structure, are not suitable for producing electrically conductive foils with a network of crystal needles.

Surprisingly, It has now been found that 6,13-dithiopentacene derivatives and unsubstituted ferrocene or specific substituted ferrocenes (hereinafter abbreviated to ferrocene derivatives), fulvalene derivatives or N-aromatic compounds form CT complexes which, unexpectedly, even in the presence of binders, crystallise in needle form, have a high conductivity and exert virtually no corrosive action on the metallic parts of processing machines. The starting compounds are also soluble in less polar organic solvents so that no very high temperatures are required for the preparation of the CT complexes. The CT complexes have an unexpectedly superior stability to moisture and heat. In addition, the CT complexes form surprisingly fine and stable crystal needles, so that films or foils with very fine-meshed needle networks and high electrical conductivity are obtained.

In one of its aspects, the invention relates to compounds of formula I

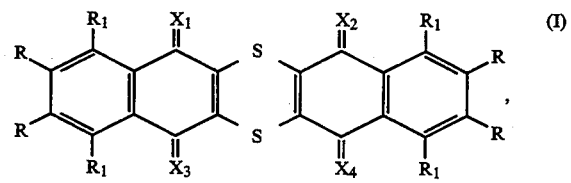

wherein the R substituents are identical and are H or $C_1$–$C_4$alkyl, or the adjacent R substituents, taken together, are —(CH$_2$)$_3$— or —(CH$_2$)$_4$—; $R_1$ is H or $C_1$–$C_4$alkyl; and $X_1$ is =N—CN, and $X_2$, $X_3$ and $X_4$ are each independently of one another =O or =N—CN.

R and $R_1$ defined as alkyl may be methyl, ethyl, n- or isopropyl or n-, iso- or tert-butyl. Preferred alkyl radicals are methyl and ethyl. In a preferred embodiment of the invention, the R substituents are $C_1$–$C_4$alkyl and the $R_1$ substituents are H, or the $R_1$ substituents are $C_1$–$C_4$alkyl and the R substituents are H. Preferably R and $R_1$ are H, methyl or ethyl. In a particularly preferred embodiment of the invention, R and $R_1$ are H.

In another preferred embodiment of the invention, $X_1$ and $X_4$ are =N—CN and $X_2$ and $X_3$ are =O or =N—CN, or $X_2$ and $X_3$ are =N—CN and $X_1$ and $X_4$ are =O or =N—CN. The most preferred meaning of $X_1$, $X_2$, $X_3$ and $X_4$ is =N—CN.

Preferred compounds of formula I are dinaphtho[2,3-b;2',3'-e][1,4]dithiine-5,7,12,14-tetracyanoimine, 2,3,9,10-tetramethyldinaphtho[2,3-b;2',3'-e][1,4]dithiine-5,7,12,14-tetracyanoimine and 2,9-dimethyldinaphtho[2,3-b;2',3'-e][1,4]dithiine-5,7,12,14-tetracyanoimine.

In another of its aspects, the invention relates to a process for the preparation of compounds of formula I, which comprises heating a tetraone of formula Ia

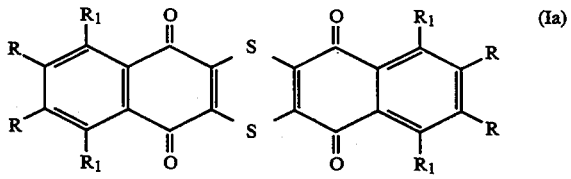

with equimolar amounts of TiCl$_4$ and [(CH$_3$)$_3$SiN]$_2$C in an inert atmosphere and in an inert solvent for 10 to 30 hours. In this process, DNDT is reacted to form dinaphtho[2,3-b;2',3'-e][1,4]dithiine-5,7,12,14-cyanoimine (6,13-dithiopentacenetetracyanoimine).

The solvent is preferably a halogenated hydrocarbon, typically dichloromethane or dichloroethane.

It is preferred to use argon as inert atmosphere.

The reaction temperature may be in the range from 0° to 100° C.

At least 1 equivalent of TiCl$_4$ and 1 equivalent of [(CH$_3$)$_3$SiN]$_2$C is used per "-one" group. It is preferred to use an excess, conveniently a 1- to 5-fold excess and, preferably, a 1- to 3-fold excess.

The preparation of 6,13-dithio-5,7,12,14-tetraone (dinaphtho[2,3-b;2',3'-e][1,4]dithiine-5,7,12,14-tetraone) is known and can be carried out, inter alia, by the process described by K. Brass and L. Köhler in Ber. Deutsch. Chem. Ges. 55, p. 2543 (1992). The corresponding substituted tetraones can be prepared in analogous manner.

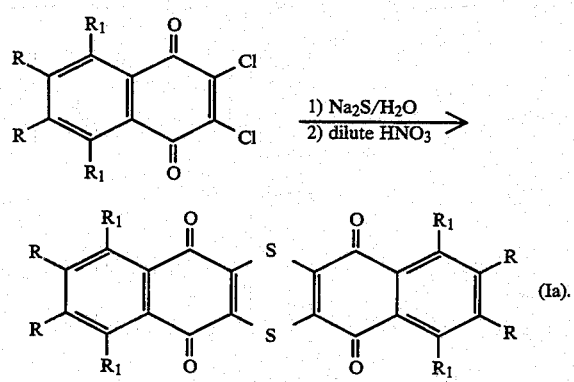

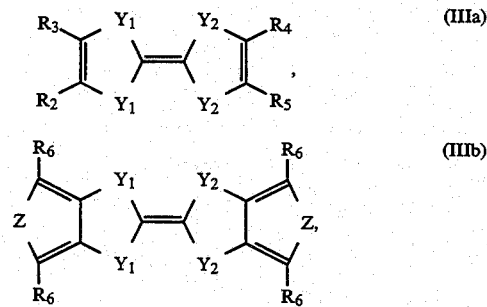

Compounds of formula I are admirably suitable for forming electrically conductive charge-transfer complexes.

In another of its aspects, the invention relates to charge-transfer complexes of formula II

wherein a) A is the radical anion of a compound of formula I or of a mixture of compounds of formula I, and b) p and q are 1, and B is the monovalent radical cation of a compound of formula IIIa or IIIb wherein $R_2$, $R_3$, $R_4$ and $R_5$ are each independently of one another H, linear or branched $C_1$–$C_{18}$alkyl-$(Z_1)_n$-, phenyl-$(Z_1)_n$- or benzyl-$(Z_1)_n$- which are unsubstituted or substituted by $C_1$–$C_4$alkyl, $C_1$–$C_4$alkoxy or $C_1$–$C_4$alkylthio, or $R_2$ and $R_3$ as well as $R_4$ and $R_5$ are independently of the other trimethylene, tetramethylene, —$Z_2$—(CH$_2$)—$Z_2$—, —$Z_2$—(CH$_2$)$_2$—$Z_2$—, —$Z_1$—CH═CH—$Z_1$— or —CH═CH—CH═CH—, each unsubstituted or substituted by $C_1$–$C_4$alkyl, $C_1$–$C_4$alkoxy or $C_1$–$C_4$alkylthio, n is 0 or 1 steht, $Y_1$ and $Y_2$ are each independently of the other —S— or —Se—, $Z_1$ is —S— or —Se—, $Z_2$ is —O—, —S— or —Se—, Z is —S—, —Se— or NR$_7$, and R$_7$ is H, $C_1$–$C_6$alkyl, phenyl or benzyl, and R$_6$ is H, $C_1$–$C_4$alkyl, phenyl or benzyl; or B is the monovalent radical cation of an N-aromatic compound containing a total of 1 to 5 unsubstituted or halogen-, $C_1$–$C_4$alkyl- or $C_1$–$C_4$alkoxy-substituted aromatic rings, at least one of which rings contains at least one —NR$_8$— or [═N$^+$R$_8$—]I$^-$ group, wherein R$_8$ is $C_1$–$C_4$alkyl or benzyl; or c) p and q are 2 and B is the divalent radical cation of an N-aromatic compound as defined above; or d) p is 2 and q is 1 and B is unsubstituted ferrocene or Fe(indenyl)$_2$ or ferrocene or Fe(indenyl)$_2$ which are substituted by $C_1$–$C_6$alkyl, $C_1$–$C_6$alkoxy, $C_1$–$C_6$hydroxyalkyl, amino-$C_1$–$C_6$alkyl, primary or secondary amino-$C_1$–$C_6$alkyl containing 1 to 12 carbon atoms in the primary amino group and 2 to 12 carbon atoms in the secondary amino group, NH$_2$, primary amino containing 1 to 12 carbon atoms, or secondary amino containing 2 to 12 carbon atoms.

R, $R_1$ and $X_1$ to $X_4$ have the same preferred meanings as indicated above.

In a preferred embodiment of the invention, $Y_1$ and $Y_2$ in the compounds of formulae III and IIIa are either —S— or —Se—, and, most preferably, —S—.

In the compounds of formula IIIa, $R_2$ and $R_3$ as well as $R_4$ and $R_5$ are preferably identical. Most preferably, $R_2$ to $R_5$ are identical.

$R_2$ to $R_5$ defined as alkyl-$(Z_1)_n$- are preferably $C_1$–$C_{12}$alkyl-$(Z_1)_n$-, more particularly $C_1$–$C_8$alkyl-$(Z_1)$-$n$ and, most preferably, $C_1$–$C_4$alkyl-$(Z_1)$-$n$. Alkyl is preferably linear alkyl. Exemplary alkyl groups are methyl, ethyl, n- and isopropyl, n-, iso- and tert-butyl, pentyl, hexyl, heptyl, octyl, nonyl, decyl, undecyl, dodecyl, tetradecyl, hexadecyl and octadecyl. Methyl, ethyl, n- and isopropyl, n-, iso- and tert-butyl are especially preferred.

In a preferred embodiment of the invention, the group alkyl-$(Z_1)_n$- is methyl, ethyl, n- and isopropyl, n-, iso- and tert-butyl, methylthio, methylseleno, ethylthio and ethylseleno.

The $C_1$–$C_4$alkyl, $C_1$–$C_4$alkoxy and $C_1$–$C_4$alkylthio substituents may typically be methyl, ethyl, n- and isopropyl, n-, iso- and tert-butyl as well as corresponding alkoxy and alkylthio radicals. Preferred substituents are methyl, ethyl, n- and isopropyl, n- and isobutyl, methoxy, ethoxy, methylthio and ethylthio.

Typical examples of the phenyl-$(Z_1)_n$- or benzyl-$(Z_1)_n$- groups are phenyl, benzyl, phenylthio, phenylseleno, benzylthio, benzylseleno, methylphenyl, methylbenzyl, ethylphenyl, n- or isopropylphenyl, n-, iso- or tert-butylphenyl, dimethylphenyl, dimethylbenzyl, methoxyphenyl, methylthiophenyl, methylthiobenzyl, methylphenylthio and methylphenylseleno.

In formula IIIb $R_6$ is preferably H or $C_1$–$C_4$alkyl. The most preferred meaning of $R_6$ is H, methyl or ethyl.

Z in formula IIIb is preferably —S— or —NR$_7$— and, most preferably, —NR$_7$—. R$_7$ is preferably H or $C_1$–$C_4$alkyl, and is most preferably H, methyl or ethyl.

$Z_1$ is preferably —S— and $Z_2$ is preferably —O— or —S—.

A preferred subgroup of the compounds of formula I comprises those compounds wherein in formula II R is H, methyl or ethyl and is most preferably H, $R_1$ is H or methyl and most preferably H, and $X_1$ to $X_4$ is ═N—CN, and, in formulae IIIa and IIIb, $R_2$ and $R_3$ as well as $R_4$ and $R_5$ or $R_2$ to $R_5$ are identical and are H, linear or branched $C_1$–$C_8$alkyl-$(Z_1)_n$-, unsubstituted or $C_1$–$C_4$alkyl-substituted phenyl-$(Z_1)_n$- or benzyl-$(Z_1)_n$-, or $R_2$ and $R_3$ and $R_4$ and $R_5$ are each together independently of the other unsubstituted or $C_1$–$C_4$alkyl-substituted trimethylene, tetramethylene, —$Z_2$—(CH$_2$)—$Z_2$—, —$Z_2$—(CH$_2$)$_2$—$Z_2$—, —$Z_1$—CH═

CH—$Z_1$— or —CH=CH—CH=CH—, n is 0 or 1, $Y_1$ and $Y_2$ are —S—, $Z_1$ is —S—, $Z_2$ is —O— or —S—, Z is —S— or $NR_7$, and $R_7$ is H or $C_1$-$C_4$alkyl, and $R_6$ is H or $C_1$-$C_4$alkyl.

A particularly preferred subgroup of the compounds of formula I comprises those compounds wherein, in formula II, R and $R_1$ are H, $X_1$ to $X_4$ are =N—CN, and in formulae IIIa and IIIb $R_2$ to $R_5$ are identical and are H, or are linear or branched $C_1$-$C_4$alkyl-$(Z_1)_n$-, or $R_2$ and $R_3$ as well as $R_4$ and $R_5$ are each together trimethylene, tetramethylene, —$Z_2$—(CH$_2$)—$Z_2$—, —$Z_2$—(CH$_2$)$_2$—$Z_2$—, —$Z_1$—CH=CH—$Z_1$— or —CH=CH—CH=CH—, n is 0 or 1, $Y_1$ and $Y_2$ are —S—, $Z_1$ is —S—, $Z_2$ is —O— or —S—, Z is —S— or $NR_7$, and $R_7$ is H or $C_1$-$C_4$alkyl, and $R_6$ is H or $C_1$-$C_4$alkyl.

Illustrative examples of CT complexes of formula I are those wherein A in formula I is 6,13-dithio-5,7,12,14-pentacenetetracyanoimine, and B is tetrathiofulvalene, tetramethyltetrathiofulvalene, tetraethyltetrathiofulvalene, dimethyldiethyltetrathiofulvalene, tetra-n-propyltetrathiofulvalene, tetra-n-butyltetrathiofulvalene, tetra(methylthio)tetrathiofulvalene, tetra(ethylthio)tetrathiofulvalene, tetra(n-propylthio)tetrathiofulvalene, tetra(n-butylthio)tetrathiofulvalene, dimethyldimethylthiotetrathiofulvalene, diethyldimethylthiotetrathiofulvalene, diethylthiodimethylthiotetrathiofulvalene and tetraselenofulvalene.

If B is the radical cation of an N-aromatic compound, the aromatic rings are hydrocarbon rings or N-heterocyclic rings containing one or two N-atoms.

An N-aromatic compound B preferably contains a total of 1 to 3 rings and at least one N-aromatic ring. In a preferred embodiment, B contains 1 to 3 rings and a heteroaromatic ring, or B is a bis-N-heteroaromatic ring. The rings are preferably 6-membered. Especially preferred N-aromatic compounds are pyridine, pyrimidine, pyrazine and phenazine.

In an especially preferred embodiment of the invention, B as N-aromatic compound in formula II corresponds to cations of formulae IVa to IVf:

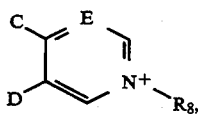   IVa

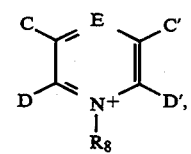   IVb

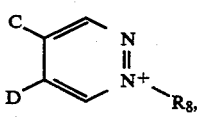   IVc

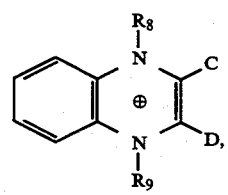   IVd

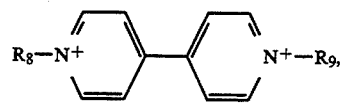   IVe

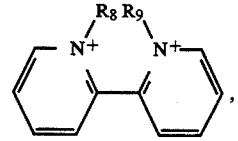   IVf wherein C, C', D and D' are H or C and D and/or C' and D' are the —CH=CH—CH=CH— group, E, N or CH, and $R_9$ independently has the same meaning as $R_8$, and $R_8$ is $C_1$-$C_4$alkyl or benzyl.

$R_8$ is preferably ethyl or methyl.

An N-aromatic compound B in formula II may typically be a cation of N-methyl- and N-ethylpyridinium; N-methyl- and N-ethylpyrazinium; N-methyl- and N-ethylquinolinium; N-methyl- and N-ethylphthalazinium; N-methyl and N-ethylisoquinolinium; N-methyl- and N-ethylbenzopyrazinium; 4,4'-dimethyl-, 4,4'-diethyl- and 4-methyl- and 4'-ethylbipyridinium; N-methyl- and N-ethylacridinium; N-methyl- and N-ethylphenazinium; 2,2'-dimethyl-, 2,2'-diethyl- and 2-methyl-, 2'-ethylbipyridinium; N-methyl- or N-ethylpyridazinium; 5,10-dimethyl-, 5,10-diethyl- or 5-methyl, 10-ethyl-5,10-dihydrophenazinium.

The compound of formula I is preferably 6,13-dithio-5,7,12,14-pentacenetetracyanoimine (dinaphtho[2,3-b;2',3'-e][1,4]dithiine-5,7,12,14-tetracyanoimine), which is in pure form, or contains up to 10% by weight, based on the entire mixture, of compound of formula I in which one or two cyanoimine groups are replaced by oxygen. Particularly preferred CT complexes of formula II are those obtained from 6,13-dithio-5,7,12,14-pentacenetetracyanoimine and N-methylpyrazinium, N-ethylpyrazinium or 5-methyl, 10-ethyl-5,10-dihydrophenazinium as B.

B as ferrocene derivative in formula II may typically be Fe[$R_{10}$]$_2$, wherein $R_{10}$ is cyclopentadienyl or indenyl which carry 1 to 5 or 1 to 7 substituents respectively selected from the group consisting of $C_1$-$C_6$alkyl, $C_1$-$C_6$alkoxy, $C_1$-$C_6$hydroxyalkyl, amino-$C_1$-$C_6$alkyl, primary or secondary amino-$C_1$-$C_6$-alkyl containing 1 to 12 carbon atoms in the primary amino group and 2 to 12 carbon atoms in the secondary amino group, $NH_2$, primary amino containing 1 to 12 carbon atoms or secondary amino containing 2 to 12 carbon atoms.

Alkyl may be linear or branched and preferably contains 1 to 4 carbon atoms. Typical examples are methyl, ethyl, n- or isopropyl, n-, iso- or tert-butyl, pentyl and hexyl. Alkyl is preferably ethyl and, most preferably, methyl.

Alkoxy may be linear or branched and preferably contains 1 to 4 carbon atoms. Typical examples are methoxy, ethoxy, n- or isopropoxy, n-, iso- or tert-butoxy, pentoxy and hexoxy. Alkoxy is preferably ethoxy and, most preferably, methoxy.

Hydroxyalkyl may be linear or branched and preferably contains 1 to 4 carbon atoms. Typical examples are hydroxymethyl, hydroxyethyl, hydroxy-n-propyl or hydroxyisopropyl, hydroxy-n-, -iso- or -tert-butyl, hydroxypentyl and hydroxyhexyl. Hydroxyalkyl is preferably hydroxyethyl and, most preferably, hydroxymethyl.

Aminoalkyl may be linear or branched and preferably contains 1 to 4 carbon atoms. Typical examples are aminomethyl, aminoethyl, n- or isoaminopropyl, n-, iso- or tert-aminobutyl, aminopentyl and aminohexyl. Aminoalkyl is preferably aminoethyl and, most preferably, aminomethyl.

Primary and secondary aminoalkyl may be linear or branched and preferably contains 1 to 4 carbon atoms. The primary amino group preferably contains one $C_1$–$C_6$alkyl group, most preferably a $C_1$–$C_4$alkyl group, and the secondary amino group preferably contains two $C_1$–$C_6$alkyl groups, most preferably one $C_1$–$C_4$alkyl group. Particularly preferred alkyl groups are methyl and ethyl. Illustrative examples of such aminoalkyl groups are methylaminomethyl, dimethylaminomethyl, diethylaminomethyl, methylaminoethyl, dimethylaminoethyl, or diethylaminopropyl, dimethylaminobutyl, diethylaminopentyl and dimethylaminohexyl. Preferred aminoalkyl groups are methylaminoethyl, dimethylaminoethyl, ethylaminoethyl, diethylaminoethyl, methylaminomethyl, dimethylaminomethyl, ethylaminomethyl and diethylaminomethyl.

Primary amino preferably contains 1 to 6 carbon atoms and secondary amino preferably contains 2 to 6 carbon atoms. Primary and secondary amino preferably contains $C_1$–$C_4$alkyl, typically methyl, ethyl, n- or isopropyl or n-, iso- or tert-butyl. Illustrative examples are methylamino, dimethylamino, ethylamino, diethylamino, n- and isopropylamino, di-n- and diisopropylamino, n-, iso- and tert-butylamino, di-n- and diisobutylamino.

In a preferred embodiment of the invention, $R_{10}$ is cyclopentadienyl or indenyl which are substituted by $C_1$–$C_4$alkyl. Most preferably, $R_{10}$ is methyl-substituted cyclopentadienyl or indenyl.

Typical examples of B are ferrocene and Fe(indenyl)$_2$ and, as ferrocene derivatives in formula II, dimethyl, tetramethyl, hexamethyl, octamethyl and decamethyl ferrocene. Preferred CT complexes of formula II are those from 6,13-dithio-5,7,12,14-pentacenetetracyanoimine and unsubstituted ferrocene, dimethyl, tetramethyl, hexamethyl, octamethyl and decamethyl ferrocene as B.

In yet another of its aspects, the invention relates to a process for the preparation of CT complexes of formula II, which comprises a) if B is unsubstituted ferrocene, a ferrocene derivative or fulvalene derivative, reacting equimolar amounts of the ferrocene, ferrocene derivative or fulvalene derivative B and of a 6,13-dithiopentacene derivative of formula I in an inert organic solvent. Equimolar amounts means that about 1 equivalent of the ferrocene or ferrocene derivative B is reacted with about 2 equivalents of the 6,13-dithiopentacene derivative of formula I to form the 2:1 complexes; or about 1 equivalent of the fulvalene or fulvalene derivative of formula IIIa or IIIb is reacted with about 1 equivalent of the 6,13-dithiopentacene derivative of formula I to form the 1:1 complexes; or b) if B is an N-aromatic compound, reacting 1 equivalent of a neutral 5,10-dihydrophenazine derivative or the iodine salt thereof as B or the iodine salt of an N-aromatic compound B with at least 1 equivalent of a 6,13-dithiopentacene derivative of formula I in an inert organic solvent. However, it can be advantageous to use an excess of dithiopentacene derivative.

The ferrocene and fulvalene derivatives are known, some are commercially available or can be prepared by standard known methods.

The N-aromatic compounds are known salts or bases, some are commercvially available or can be prepared by standard known methods. Reaction of the neutral base B and the alkyl iodide gives the desired iodine salt. The preparation of these derivatives is described by L. Russell Melby in Can. J. Chem. Vol. 43, pp. 1448–1453 (1965).

The inventive process for the preparation of the CT complexes is conveniently carried out at elevated temperature, typically in the range from room temperature to 150° C. To isolate the novel CT complexes, the reaction mixture can be cooled and the precipitated crystals isolated by filtration and purified by washing and/or recrystallisation.

Suitable solvents are typically non-polar, polar and aprotic solvents which may be used singly or in mixtures of at least two solvents. Typical examples are: ethers (anisole, dibutyl ether, tetrahydrofuran, dioxane, ethylene glycol monomethyl or dimethyl ether, ethylene glycol monoethyl or diethyl ether, diethylene glycol diethyl ether, triethylene glycol dimethyl ether), halogenated hydrocarbons (methylene chloride, chloroform, 1,2-dichlorethane, 1,1,1-trichloroethane, 1,1,2,2-tetrachloroethane), carboxylates and lactones (ethyl acetate, methyl propionate, ethyl benzoate, 2-methoxyethylacetate, γ-butyrolactone, δ-valerolactone, pivalolactone), carboxamides and lactams (N,N-dimethylformamide, N,N-diethylformamide, N,N-dimethylacetamide, tetramethylurea, hexamethylphosphoric triamide, γ-butyrolactam, ε-caprolactam, N-methylpyrrolidone, N-acetylpyrrolidone, N-methylcaprolactam), ketones (methyl ethyl ketone, methyl isobutyl ketone), sulfoxides (dimethyl sulfoxide), sulfones (dimethyl sulfone, diethyl sulfone, trimethylene sulfone, tetramethylene sulfone), tertiary amines (N-methylpiperidine, N-methylmorpholine), substituted benzenes (benzonitrile, chlorobenzene, o-dichlorobenzene, 1,2,4-trichlorobenzene, nitrobenzene, toluene, xylene), nitriles (acetonitrile, propionitrile) and aliphatic or cycloaliphatic hydrocarbons (petroleum ether, pentane, hexane, cyclohexane and methylcyclohexane). Suitable solvents are also aromatic-aliphatic ethers, for example methyl or ethyl phenyl ether.

Polar solvents are preferred if B is an N-aromatic compound, because the iodine salts of compounds B have better solubility under these conditions. Preferred polar solvents are typically dimethyl formamide and γ-butyrolactam.

The CT complexes obtainable by the process of this invention are obtained in great purity and, after filtration, need only be washed with solvents. Ordinarily they are obtained as dark coloured to black needle-shaped crystals which have pressed pellet conductivities of more than $10^{-4}$ S/cm. They therefore have excellent suitability for use as electric conductors. Depending on the type of CT complex and on the amount added it is possible to obtain electrically conductive or antistatically treated polymers by incorporating these CT complexes in polymer materials, the CT complex being present in the polymer matrix as a network of crystal needles. Depending on the concentration of CT complex in the polymer matrix, very fine meshed needle networks can be obtained.

In yet another of its aspects, the invention relates to a composition comprising a) a thermosetting, thermoplastic or structurally crosslinked polymer and b) a CT complex of formula II in the form of a network of crystal needles in the polymer matrix.

The novel compositions may contain the CT complex in a concentration of 0.01 to 30% by weight, preferably of 0.01 to 20% by weight, more particularly of 0.01 to 10% by weight and, most preferably, of 0.1 to 5% by weight, based on said composition.

The thermoplastic polymers may conveniently be selected from among the following polymers, copolymers or mixtures of these polymers:

1. Polymers of monoolefins and diolefins, for example polypropylene, polyisobutylene, polybut-1-ene, polymethylpent-1-ene, polyisoprene or polybutadiene, as well as polymers of cycloolefins, for example of cyclopentene or norbornene, polyethylene (which can be uncrosslinked or crosslinked), for example high density polyethylene (HDPE), low density polyethylene (LDPE), linear low density polyethylene (LLDPE), branched low density polyethylene (BLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, ethylene/hexene copolymers, ethylene/ethylpentene copolymers, ethylene/heptene copolymers, ethylene/octene copolymers, propylene/isobutylene copolymers, ethylene/but-1-ene copolymers, propylene/butadiene copolymers, isobutylene/isoprene copolymers, ethylene/alkyl acrylate copolymers, ethylene/alkyl methacrylate copolymers, ethylene/vinyl acetate or ethylene/acrylic acid copolymers and the salts thereof (ionomers), as well as terpolymers of ethylene with propylene and a diene, such as hexadiene, dicyclopentadiene or ethylidene-norbornene; and also mixtures of such polymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

3a. Hydrocarbon resins (for example C5–C9) including hydrogenated modifications thereof (for example tackifiers) and mixtures of polyalkylenes and starch.

4. Polystyrene, poly(p-methylstyrene), poly(α-methylstyrene).

5. Copolymers of styrene or α-methylstyrene with dienes or acrylic derivatives, for example styrene/butadiene, styrene/acrylonitrile, styrene/alkyl methacrylate, styrene/maleic anhydride, styrene/butadiene/alkyl acrylate, styrene/butadiene/alkyl methacrylate styrene/acrylonitrile/methyl acrylate; mixtures of high impact strength from styrene copolymers and another polymer, for example from a polyacrylate, a diene polymer or an ethylene/propylene/diene terpolymer; and block copolymers of styrene, for example styrene/butadiene/styrene, styrene/isoprene/styrene, styrene/ethylene/butylene/styrene or styrene/ethylene/propylene/styrene.

6. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed in 5), for example the copolymer mixtures known as ABS, MBS, ASA or AES polymers.

7. Halogen-containing polymers, such as polychloroprene, chlorinated rubbers, chlorinated or chlorosulfonated polyethylene, copolymers of ethylene and chlorinated ethylene, epichlorohydrin homo- and copolymers, polymers of halogenated vinyl compounds, for example polyvinyl chloride, polyvinylidene chloride, polyvinyl fluoride, polyvinylidene fluoride, as well as copolymers thereof, for example vinyl chloride/vinylidene chloride, vinyl chloride/vinyl acetate or vinylidene chloride/vinyl acetate copolymers.

8. Polymers derived from α,β-unsaturated acids and derivatives thereof, such as polyacrylates and polymethacrylates, polymethyl methacrylate impact-modified with butyl acrylate, polyacrylamides and polyacrylonitrile.

9. Copolymers of the monomers mentioned in 8) with each other or with other unsaturated monomers, for example acrylonitrile/butadiene, acrylonitrile/alkyl acrylate, acrylonitrile/alkoxyalkyl acrylate or acrylonitrile/vinyl halide copolymers or acrylonitrile/alkyl methacrylate/butadiene terpolymers.

10. Polymers derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

11. Homopolymers and copolymers of cyclic ethers, such as polyalkylene glycols, polyethylene oxide, polypropylene oxide or copolymers thereof with bis(glycidyl) ethers.

12. Polyacetals such as polyoxymethylene and those polyoxymethylenes which contain ethylene oxide as a comonomer, polyacetals modified with thermoplastic polyurethanes, acrylates or MBS.

13. Polyphenylene oxides and sulfides and mixtures thereof with styrene polymers or polyamides.

14. Polyurethanes derived from polyethers, polyesters or hydroxyl-terminated polybutadienes on the one hand and aliphatic or aromatic polyisocyanates on the other, as well as precursors thereof.

15. Polyamides and copolyamides derived from diamines and dicarboxylic acids and/or from aminocarboxylic acids or the corresponding lactams, such as polyamide 4, polyamide 6, polyamide 6/6, 6/10, 6/9, 6/12, 4/6, 12/12, polyamide 11, polyamide 12, aromatic polyamides obtained by condensation of m-xylene diamine and adipic acid; polyamides prepared from hexamethylenediamine and isophthalic or/and terephthalic acid and optionally an elastomer as modifier, for example poly-2,4,4,-trimethylhexamethylene terephthalamide or poly-m-phenylene isophthalamide; and also copolymers of the aforementioned polyamides with polyolefins, olefin copolymers, ionomers or chemically bonded or grafted elastomers; or with polyethers, as with polyethylene glycols, polypropylene glycols or polytetramethylene glycols; polyamides or copolyamides modified with EPDM or ABS; polyamides condensed during processing (RIM polyamide systems).

16. Polyureas, polyimides, polyamide-imides and polybenzimidazoles.

17. Polyesters derived from dicarboxylic acids and diols and/or from hydroxycarboxylic acids or the corresponding lactones, such as polyethylene terephthalate, polybutylene terephthalate, poly-1,4-dimethylolcyclohexane terephthalate, poly[2,2,-(4-hydroxyphenyl)-propane] terephthalate and polyhydroxybenzoates as well as block copolyether esters derived from hydroxyl-terminated polyethers; and also polyester modified with polycarbonates or MBS.

18. Polycarbonates and polyester carbonates.

19. Polysulfones, polyether sulfones and polyether ketones.

20. Polyethers of digylcidyl compounds, typically diglycidyl ethers and diols, e.g. of the diglycidyl ether of bisphenol A and bisphenol A.

21. Natural polymers, such as cellulose, rubber, gelatin and chemically modified homologous derivatives thereof, such as cellulose acetates, cellulose propionates and cellulose butyrates, or the cellulose ethers such as methyl cellulose; as well as rosins and their derivatives.

22. Blends of the aforementioned polymers (polyblends), for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 66 and copolymers, PA/HDPE, PA/PP, PA/PPO.

Preferred thermoplastic polymers are polyolefins, polystyrene, polyvinyl chloride, polyvinylidene chloride, polyvinylidene fluoride, polyacrylates, polymethacrylates, polyamides, polyesters, polycarbonates, aromatic polysulfones, aromatic polyethers, aromatic polyether sulfones, polyimides and polyvinyl carbazole.

The thermosetting and structurally crosslinked polymers may be typically the following polymers:

1. Crosslinked polymers which are derived from aldehydes on the one hand and phenols, ureas and melamines on the other hand, such as phenol/formaldehyde resins, urea/formaldehyde resins and melamine/formaldehyde resins.

2. Drying and non-drying alkyd resins.

3. Unsaturated polyester resins which are derived from copolyesters of saturated and unsaturated dicarboxylic acids with polyhydric alcohols and vinyl compounds as crosslinking agents, and also halogen-containing modifications thereof of low flammability.

4. Crosslinkable acrylic resins derived from substituted acrylic esters such as epoxy acrylates, urethane acrylates or polyester acrylates.

5. Alkyd resins, polyester resins or acrylate resins which are cross-linked with melamine resins, urea resins, polyisocyanates or epoxy resins.

6. Rubber derived from crosslinked polydienes, for example butadiene or isoprene; silicon rubber.

7. Epoxy resins which are derived from polyepoxides, for example from bisglycidyl ethers or from cycloaliphatic diepoxides, and which may contain a hardener as crosslinking agent or which are crosslinked thermally using curing accelerators or by irradiation.

Among the crosslinked polymers, crosslinked epoxy resins are preferred which, as polyepoxides, are derived preferably from glycidyl compounds which contain on average two epoxy groups in the molecule. Particularly suitable glycidyl compounds are those which contain two glycidyl groups, β-methylglycidyl groups or 2,3-epoxycyclopentyl groups attached to a hetero atom (e.g. sulfur, preferably oxygen or nitrogen), in particular bis(2,3-epoxycyclopentyl) ether; diglycidyl ethers of polyhydric aliphatic alcohols, such as 1,4-butanediol, or polyalkylene glycols, such as polypropylene glycols; diglycidyl ethers of cycloaliphatic polyols, such as 2,2-bis(4-hydroxycyclohexyl)propane; diglycidyl ethers of polyhydric phenols, such as resorcinol, bis(p-hydroxyphenyl)methane, 2,2-bis-(p-hydroxyphenyl)propane (=diomethane), 2,2-bis(4'-hydroxy-3',5'-dibromophenyl)propane, 1,3-bis(p-hydroxyphenyl)ethane; bis(β-methylglycidyl) ethers of the above dihydric alcohols or dihydric phenols; diglycidyl esters of dicarboxylic acids, such as phthalic acid, terephthalic acid, Δ4-tetrahydrophthalic acid and hexahydrophthalic acid; N,N-diglycidyl derivatives of primary amines and amides and heterocyclic nitrogen bases which contain two N-atoms, and N,N'-diglycidyl derivatives of disecundary diamides and diamines, such as N,N-diglycidylaniline, N,N-diglycidyltoluidine, N,N-diglycidyl-p-aminophenyl methyl ether, N,N'-dimethyl-N,N'-diglycidylbis(p-aminophenyl)methane; N',N''-diglycidyl-N-phenyl-isocyanurate; N,N'-diglycidyl ethyleneurea; N,N'-diglycidyl-5,5-dimethylhydantoin, N,N'-diglycidyl-5-isopropyl-hydantoin, N,N-methylenebis-(N',N'-diglycidyl-5,5-dimethylhydantoin), 1,3-bis(N-glycidyl-5,5-dimethylhydantoin)-2-hydroxypropane; N,N'-diglycidyl-5,5-dimethyl-6-isopropyl-5,6-dihydrouracil, triglycidyl isocyanurate.

A preferred group of epoxy resins comprises glycidylated novolaks, hydantoins, aminophenols, bisphenols and aromatic diamines or cycloaliphatic epoxy compounds. Particularly preferred epoxy resins are glycidylated cresol novolaks, bisphenol A and bisphenol F diglycidyl ether, hydantoin-N,N'-bisglycide, p-aminophenol triglycide, diaminodiphenylmethane tetraglycide, vinylcyclohexene dioxide, 3,4-epoxycyclohexylmethyl-3,4-epoxycyclohexanecarboxylate or mixtures thereof.

Further suitable epoxy resins are prereacted adducts of such epoxy compounds with epoxy hardeners, for example an adduct of a diglycidyl ether of bisphenol A and bisphenol A, or adducts which have been prereacted with oligoesters which carry two terminal carboxyl groups and epoxides.

Suitable hardeners for epoxy resins are acidic or basic compounds. Illustrative examples of suitable hardeners are: polyhydric phenols (resorcinol, 2,2-bis(4-hydroxyphenyl)propane) or phenol-formaldehyde resins; polybasic carboxylic acids and the anhydrides thereof, such as phthalic anhydride, tetrahydrophthalic anhydride, hexahydrophthalic anhydride, 4-methylhexahydrophthalic anhydride, 3,6-endomethylene-tetrahydrophthalic anhydride, 4-methyl-3,6-endomethylen-tetrahydrophthalic anhydride (methylnadic anhydride), 3,4,5,6,7,7-hexachloroendomethylene-tetrahydrophthalic anhydride, succinic anhydride, adipic anhydride, trimethyladipic anhydride, sebacic anhydride, maleic anhydride, dodecylsuccinic anhydride, pyromellitic dianhydride, trimellitic anhydride, benzophenonetetracarboxylic dianhydride, or mixtures of such anhydrides.

A preferred group of hardeners comprises novolaks and polycarboxylic anhydrides.

The epoxy resins can also be additionally cured with curing accelerators or only with thermal curing catalysts. Exemplary of curing accelerators and catalysts are 3-ethyl-4-methylimidazole, triamylammonium phenolate; mono- or polyphenols (phenol, diomethane, salicylic acid); boron trifluoride and the complexes thereof with organic compounds, such as boron trifluoride ether complexes and boron trifluoride amine complexes ($BF_3$/monoethylamine complex); phosphoric acid and triphenylphosphite.

Curing accelerators and catalysts are normally added in an mount of 0.1 to 10% by weight, based on the epoxy resin. Hardeners for epoxy resins are normally used in equimolar amounts, based on the epoxy groups and functional groups of a hardener.

Further additives for enhancing processing properties, the mechanical, electrical and thermal properties, surface properties and light stability can be blended into the novel formulation. Exemplary of such additives are finely particulate fillers, reinforcing fillers, plasticisers, lubricants and mould release agents, adhesion promoters, antistatic agents, antioxidants, heat and light stabilisers, pigments and dyes.

In a preferred embodiment of the invention, the novel compositions are shaped to mouldings, films, foils, fibres, or to coatings on at least one surface of a substrate.

In yet another of its aspects, the invention relates to a process for the preparation of novel compositions, which comprises (a) blending a CT complex of formula II into a thermoplastic polymer, (b) blending a CT complex of formula II with at least one component of a thermosetting or structurally crosslinkable polymer and then polymerising the blend, together with a further optional component, to a thermosetting or structurally crosslinked polymer, or (c) dissolving a compound of formula I or ferrocene or a ferrocene derivative B, a fulvalene derivative of formula IIIa or IIIb as B, a 5,10-dihydrophenazine derivative or the iodine salt thereof as B or the iodine salt of an N-aromatic compound B, together with a thermoplastic polymer or with at least one component of a thermosetting or structurally crosslinkable polymer in an organic solvent, mixing this solution, together with further optional components of a thermosetting or structurally crosslinkable polymer with a solution of ferrocene or ferrocene derivative B, a fulvalene derivative of formula IIIa or IIIb as B, a 5,10-dihydrophenazine derivative or the iodine salt thereof as B or the iodine salt of an N-aromatic compound B or a compound of formula I, removing the solvent and polymerising curable mixtures to a thermosetting or structurally crosslinked polymer. The process can be combined with a shaping process.

The novel compositions can be prepared by methods known in plastics technology. In shaping techniques for polymers, typically casting, compression moulding, injection moulding and extrusion, the CT complex itself can be added to a thermoplastic polymer or to at least one component of a thermosetting plastic to form a suspension, or separately to each component (e.g. the epoxy resin and the hardener) to form a solution or suspension, such that, after shaping, the CT complex crystallises and precipitates in the form of needles upon cooling and the needles form a network in a polymer matrix.

In a particularly preferred embodiment of the invention, the novel composition is in the form of a film or foil or a coating on at least one surface of a substrate. Such embodiments are conveniently prepared by suspending and/or dissolving a thermoplastic polymer or at least one starting material of a thermosetting polymer or a structurally crosslinked polymer in an inert solvent together with a CT complex of formula II, or dissolving a thermoplastic polymer or at least one starting material of a thermosetting polymer or a structurally crosslinked polymer together with a compound of formula I or ferrocene or a ferrocene derivative B, a fulvalene derivative B or an iodine salt of an N-aromatic compound B, and then mixing the solution or suspension with a solution of the ferrocene or ferrocene derivative B, a fulvalene derivative B or the N-aromatic iodine salt B or a compound of formula I, and subsequently applying the mixture by known coating techniques to a substrate which may be preheated, and thereafter removing the solvent by heating, such that crosslinkable mixtures can then be fully cured. Self-supporting films and foils are obtained by peeling the coating from the substrate or by extrusion.

Examples of suitable substrates are glass, metals, plastics, mineral and ceramic materials, wood and paper. The substrates may be of any external shape and are typically mouldings, filaments, fibres, fabrics, bars, pipes, ribbons, sheets, boards, rolls or casings.

Suitable coating techniques are typically brushing, rolling, doctor coating, casting, spin coating, curtain coating and spraying. Spraying methods are especially preferred, as on the one hand very thin and uniform layers with substantially isotropic, very fine-mesh and homogeneous networks are obtainable from crystal needles of the CT complexes and, on the other, the size of the crystal needles and the mesh width of the networks can be controlled by the droplet size, even when suspensions are sprayed.

Suitable inert solvents for polymers and starting materials for polymers are typically polar and, preferably, aprotic solvents, which may be used singly or in mixtures of at least two solvents. Representative examples of such solvents are: ethers (ansiole, dibutyl ether, tetrahydrofuran, dioxane, ethylene glycol monomethyl or dimethyl ether, ethylene glycol monoethyl or diethyl ether, diethylene glycol diethyl ether, triethylene glycol dimethyl ether), halogenated hydrocarbons (methylene chloride, chloroform, 1,2-dichloroethane, 1,1,1-trichloroethane, 1,1,2,2-tetrachloroethane), carboxylates and lactones (ethyl acetate, methyl propionate, ethyl benzoate, 2-methoxyethyl acetate, $\gamma$-butyrolactone, $\delta$-valerolactone, pivalolactone), carboxamides and lactams (N,N-dimethylformamide, N,N-diethylformamide, N,N-dimethylacetamide, tetramethylurea, hexamethylphosphoric triamide, $\gamma$-butyrolactam, $\epsilon$-caprolactam, N-methylpyrrolidone, N-acetylpyrrolidone, N-methylcaprolactam), sulfoxides (dimethyl sulfoxide), sulfones (dimethyl sulfone, diethyl sulfone, trimethylene sulfone, tetramethylene sulfone), tertiary amines (N-methylpiperidine, N-methylmorpholine) substituted benzenes (benzonitrile, chlorobenzene, o-dichlorobenzene, 1,2,4-trichlorobenzene, nitrobenzene, toluene, xylene) and nitriles (acetonitrile, propionitrile). Further suitable solvents are aromatic-aliphatic ethers such as methyl or ethyl phenyl ether as well as ketones such as acetone, methyl ethyl ketone, methyl propyl ketone, methyl butyl ketone, dipropyl ketone, dibutyl ketone and methyl isobutyl ketone. Suitable solvents for the compounds of formula II and the N-aromatic compounds/iodine salts B have been mentioned hereinabove.

The coating techniques can conveniently be carried out by dissolving the individual components separately and combining them just before application of the chosen technique. However, it is also possible to prepare two solutions of the components, for example of polymer solution and ferrocene or ferrocene derivative B, fulvalene derivative B or N-aromatic compound/iodine salt B or compound of formula I, and solution of a compound of formula I or ferrocene or ferrocene derivative or fulvalene derivative B or N-aromatic compound/iodine salt B, optionally together with a polymer, or to combine all the components in one solution. In this last mentioned case, the CT complexes can crystallise out already prior to coating; but this has virtually no effect on the desired quality of the coating.

The solutions are preferably heated, conveniently to 30°–200° C. It is useful to heat the substrate as well to accelerate the removal of the solvent, which is normally effected in the temperature range from 50° to 150° C., preferably 50° to 100° C., until the coating is dry. If it is desired to detach the coatings to give self-supporting films or sheets, the substrate can be treated with antiblocking agents prior to coating.

An alternative coating method comprises suspending the CT complexes, which are obtained as needle-shaped crystals, in a solution of a polymer or of starting materials for thermosetting polymers, then coating a substrate and afterwards removing the solvent, and, if appropriate, thereafter effecting a cure to form the thermosetting polymers. It is also possible to prepare dry powder mixtures from polymer powders or solid starting materials for thermosetting polymers and the CT complexes, and to process these mixtures in coating or electrostatic coating methods to layers on substrates. Networks of crystal needles in a polymer matrix are also obtained in these alternative methods.

It is also possible to produce pure layers of networks of crystal needles of the CT complexes on a substrate by applying to a substrate solutions or suspensions of the CT complexes in a solvent and afterwards evaporating the solvent. Such layers can be electrochemically metallised to enhance the conductivity, conveniently with Cu, Pt or Pd. It can be useful to provide such pure layers with a protective coating of a polymer or to coat the pure layers subsequently with a polymer.

The layer thicknesses can vary over a wide range, depending on the choice of coating method. Spray methods give very thin layers, whereas thicker layers can also be obtained with brushing and casting methods. The layer thicknesses can be typically from 0.01 to 5000 $\mu$m, preferably from 0.1 to 1000 $\mu$m and, most preferably, from 0.1 to 500 $\mu$m.

Depending on the choice of polymer, the novel compositions are opaque or transparent and have outstanding electrical properties. Thus, surprisingly, the coatings and mouldings have an excellent discharge capacity which, for heterogeneous materials, is otherwise difficult to achieve or cannot be achieved at all. The compositions are therefore especially suitable for use for making antistatically treated moulded parts for the electrostatic screening of components or for making antistatically treated mouldings. The high conductivities also permit the use of the novel compositions as electric conductors, for example as electrodes for display elements or electronic components as well as charge carriers in capacitors. The compositions also have excellent mechanical strength and performance properties. The compositions can also be prepared at comparatively low temperatures and have the additional advantage of causing no or only insignificant corrosion in metallic machine parts. Furthermore, they have good stability to the action of heat and/or moisture.

Further objects of the invention are the use of the novel charge transfer complexes of formula I as electric conductors; the use of the novel compounds of formula I for the preparation of charge transfer complexes; the use of the novel charge transfer complexes of formula II as electric conductors; the use of the novel compositions as antistatically treated moulded parts for the electronic screening of components or as antistatically treated mouldings; the use of the novel compositions as electric conductors; the use of the novel compositions as electrode material; and the use of the novel compositions in the form of films or foils as charge carders in capacitors.

Dinaphtho[2,3-b;2',3'-e][1,4]dithiine-5,7,12,14-tetracyanoimine (6,13-dithio-5,7,12,14-pentacenetetracyanoimine) has four reversible reduction potentials, measured in DMF, 0.1 mol $(C_4H_9)_4NBF_4$ at 50 mV/s: +0.322, +0.122, −0.390 and −0.600 V, based on the standard calomel electrode (SCE). 6,13-Dithiopentacenetetracyanoimine is thus a particularly strong electron acceptor compared with TCNQ or 5,7,12,14-pentacenetetracyanoimine and is able to form CT complexes with a greater range of donors. Dinaphtho[2,3-b;2',3'-e][1,4]dithiine-5,7,12,14-tetracyanoimine intrinsically has a conductivity at room temperature of $3.3 \cdot 10^{-7}$ S/cm as pressed pellet.

The following Examples illustrate the invention in more detail.

A) PREPARATION OF THE ACCEPTOR MOLECULES

Example A1: Preparation of 6,13-Dithio-5,7,12,14-pentacenetetracyanoimine (dinaphtho[2,3-b;2',3'-e][1,4]dithiine-5,7,12,14-tetracyanoimine)

2.52 g (13.28 mmol) of $TiCl_4$ are added dropwise to a suspension of 0.5 g (1.33 mmol) of DNDT in 50 ml of dichloromethane under argon. After stirring for 1 h, 2.97 g (15.94 mmol) of bis(trimethylsilylcarbodiimide) $([(CH_3)_3SiN]_2C)$ are added. The reaction mixture is refluxed for 20 h under argon to give a dark red suspension. The mixture is cooled, poured on to 50 g of ice and extracted with 100 ml of dichloromethane. The organic layer is separated, dried over $Na_2SO_4$ and filtered. The solvent is removed to leave a dark green residue (0.08 g). The aqueous suspension is filtered to give 0.58 g of a dark green residue. The two portions are combined and refluxed in 200 ml of anisole for 15 min. The dark red solution is filtered and cooled to room temperature, whereupon fine black needles form. The needles are isolated by filtration and washed with pentane, giving 370 mg of the title compound. Elemental analysis: found (calcd) for $C_{24}H_8N_8S_2 \cdot 1.2$ anisole: C 64.31 (64.61); H 3.02 (2.95); N 18.44 (18.60); S 10.93 (10.60).

Example A2: Preparation of 2,3,9,10-Tetramethyldinaphtho[2,3-b;2',3'-e][1,4]dithiine-5,7,12,14-tetracyanoimine 2.52 g (13.28 mmol) of TiCl$_4$ are added to a suspension of 0.58 g (1.33 mmol) of 2,3,9,10-tetramethyldinaphtho[2,3-b;2',3'-e][1,4]dithiine-5,7,12,14-tetrone in 50 ml of dichloromethane under argon. After stirring for 15 min, 2.97 g (15.94 mmol) of [(CH$_3$)$_3$SiN]$_2$C are added. The reaction mixture is refluxed for 16 h under argon. After cooling, the mixture is poured on to 100 ml of ice and extracted with 100 ml of dichloromethane. The organic layer is separated, dried over Na$_2$SO$_4$ and filtered. The solvent is removed by evaporation, leaving a dark green residue (0.4 g). The aqueous suspension is filtered to give 0.35 g of a dark green residue. The two solid portions are combined and dissolved in 300 ml of refluxing anisole over 15 min. The dark red solution is filtered and cooled to room temperature. Black needles are precipitated by addition of diethyl ether. The needles are isolated by filtration and washed with pentane, giving 0.25 g of the title compound. Elemental analysis: found (calcd) for C$_{28}$H$_{16}$N$_8$S$_2$.0.5 anisole: C 63.60 (64.92); H 3.56 (3.47); N 18.30 (19.23); S 11.07 (11.00).

Example A3: Preparation of 2,9-Dimethyldinaphtho[2,3-b;2',3'-e][1,4]dithiine-5,7,12,14-tetracyanoimine 8.82 g (46.48 mmol) of TiCl$_4$ are added to a suspension of 1.88 g (4.65 mmol) of 2,9-dimethyldinaphtho[2,3-b;2',3'-e][1,4]dithiine5,7,12,14-tetrone in 100 ml of dichloromethane under argon. After stirring for 15 min, 10.40 g (55.78 mmol) of [(CH$_3$)$_3$SiN]$_2$C are added. The reaction mixture is refluxed for 16 h under argon. The mixture is cooled, poured on to 100 ml of ice and extracted with 100 ml of dichloromethane. The organic layer is separated, dried over Na$_2$SO$_4$ and filtered. The solvent is removed by evaporation to leave a dark green residue (1.66 g). The residue is dissolved in 300 ml of trichlorobenzene, and the solution is filtered and cooled to room temperature. Brown needles are precipitated by addition of diethyl ether. The needles are filtered and washed with pentane to give 0.75 g of the title compound. Elemental analysis: found (calcd) for C$_{26}$H$_{12}$N$_8$S$_2$.0.7 ether: C 61.94 (62.62); H 3.20 (3.47); N 19.75 (20.28); S 11.60 (11.60). Alternating current in 0.1M Bu$_4$NBF$_4$ solution in dichloromethane measured at 50 mV/s: +0.327; +0.075; −0.375; −0.615 V based on the SCE.

B) PREPARATION OF CT COMPLEXES

Example B1: Preparation of a CT Complex from Hexamethylferrocene and 6,13-Dithio-5,7,12,14-pentacenetetracyanoimine To a 150° C. hot solution of 100 mg (0.212 mmol) of 6,13-dithio-5,7,12,14-pentacenetetracyanoimine in 50 ml of anisole is added an equally hot solution of 28.6 mg (0.106 mmol) of hexamethyl ferrocene in 5 ml of anisole. The resultant solution is cooled and the CT complex is isolated by filtration. The precipitated dark-brown of crystal needles are washed with pentane and then dried under a high vacuum, affording 66 mg of the title compound with a pressed pellet electrical conductivity (measured by the four-point method) of 0.35 S/cm; m.p. 214° C. Elemental analysis: found (calcd) for C$_{64}$H$_{38}$N$_{16}$S$_4$Fe: C 63.05 (63.26); H 3.34 (3.15); N 18.08 (18.44); Fe 4.08 (4.60); S 10.69 (10.55).

Example B2: Preparation of a CT Complex from Dimethyl Ferrocene and 6,13-Dithio-5,7,12,14-pentacenetetracyanoimine To a 150° C. hot solution of 100 mg (0.212 mmol) 6,13-dithio-5,7,12,14-pentacenetetracyanoimine in 50 ml of anisole is added an equally hot solution of 23 mg (0.106 mmol) of dimethyl ferrocene in 5 ml of anisole. The resultant solution is cooled and the CT complex is isolated by filtration. The precipitated dark-brown of crystal needles are washed with pentane and then dried under a high vacuum, affording 66 mg of the title compound with a pressed pellet electrical conductivity of 1.17 S/cm; m.p. 192° C. Elemental analysis: found (calcd) for C$_{60}$H$_{30}$N$_{16}$S$_4$Fe: C 62.38 (62.17); H 2.76 (2.61); N 18.05 (19.33); Fe 4.87 (4.82); S 10.95 (11.07).

Example B3: Preparation of a CT Complex from Tetrathiofulvalene and 6,13-Dithio-5,7,12,14-pentacenetetracyanoimine To a 150° C. hot solution of 100 mg (0.212 mmol) 6,13-dithio-5,7,12,14-pentacenetetracyanoimine in 50 ml of anisole is added an equally hot solution of 43 mg (0.212 mmol) of tetrathiofulvalene in 5 ml of anisole. The resultant solution is cooled and the CT complex is isolated by filtration. The precipitated black crystal needles are washed with pentane and then dried under a high vacuum, affording 93 mg of the title compound with a pressed pellet electrical conductivity of 0.20 S/cm; m.p. 229° C. Elemental analysis: found (calcd) for C$_{30}$H$_{12}$N$_8$S$_6$+0.5 anisole: C 53.61 (55.05); H 2.16 (2.21); N 14.97 (15.33); S 27.21 (26.32).

Example B4: Preparation of a CT Complex From Tetramethyltetrathiofulvalene and 6,13-Dithio-5,7,12,14-pentacenetetracyanoimine To a 150° C. hot solution of 100 mg (0.212 mmol) 6,13-dithio-5,7,12,14-pentacenetetracyanoimine in 50 ml of anisole is added an equally hot solution of 55 mg (0.212 mmol) of tetramethyltetrathiofulvalene in 5 ml of anisole. The resultant solution is cooled and the CT complex is isolated by filtration. The precipitated black crystal needles are washed with pentane and then dried under a high vacuum, affording 87 mg of the title compound with a pressed pellet electrical conductivity of 1.04 S/cm; m.p. 198° C. Elemental analysis: found (calcd) for C$_{34}$H$_{20}$N$_8$S$_6$+0.5 anisole: C 58.10 (58.65); H 2.77 (2.56); N 17.21 (17.79); S 20.81 (20.36).

What is claimed is:

1. A compound of formula I

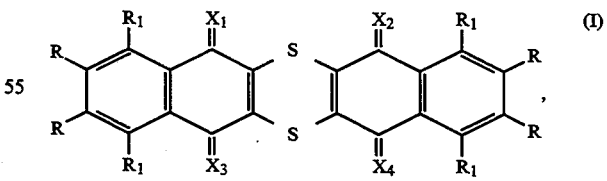

wherein the R substituents are identical and are H or C$_1$–C$_4$alkyl, or the adjacent R substituents, taken together, are —(CH$_2$)$_3$— or —(CH$_2$)$_4$—; R$_1$ is H or C$_1$–C$_4$alkyl; and X$_1$ is =N—CN, and X$_2$, X$_3$ and X$_4$ are =O or =N—CN.

2. A compound of formula I according to claim 1, wherein R is C$_1$–C$_4$alkyl and R$_1$ is H.

3. A compound of formula I according to claim 1, wherein R$_1$ is C$_1$–C$_4$alkyl and R is H.

4. A compound of formula I according to claim 1, wherein R and $R_1$ as alkyl are methyl or ethyl.

5. A compound of formula I according to claim 1, wherein R and $R_1$ are H, methyl or ethyl.

6. A compound of formula I according to claim 1, wherein R and $R_1$ are H.

7. A compound of formula I according to claim 1, wherein $X_1$ and $X_4$ are =N—CN and $X_2$ and $X_3$ are =O or =N—CN, or $X_2$ and $X_3$ are =N—CN and $X_1$ and $X_4$ are =O or =N—CN.

8. A compound of formula I according to claim 1, wherein $X_1$, $X_2$, $X_3$ and $X_4$ are =N—CN.

9. A compound of formula I according to claim 1 which is dinaphtho[2,3-b;2',3'-e][1,4]dithiine-5,7,12,14-tetracyanoimine.

10. A compound of formula I according to claim 1 which is 2,3,9,10-tetramethyldinaphtho[2,3-b;2',3'-e][1,4]dithiine-5,7,12,14-tetracyanoimine.

11. A compound of formula I according to claim 1 which is 2,9-dimethyldinaphtho[2,3-b;',3'-e][1,4]dithiine-5,7,12,14-tetracyanoimine.

12. A process for the preparation of a compound of formula I

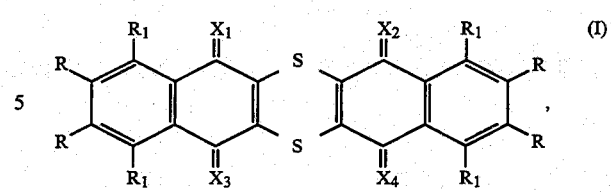

wherein the R substituents are identical and are H or $C_1$-$C_4$alkyl, or the adjacent R substituents, taken together, are —(CH$_2$)$_3$— or —(CH$_2$)$_4$—; $R_1$ is H or $C_1$-$C_4$alkyl; and $X_1$ is =N—CN, and $X_2$, $X_3$ and $X_4$ are =O or =N—CN, which comprises heating a tetraone of formula Ia

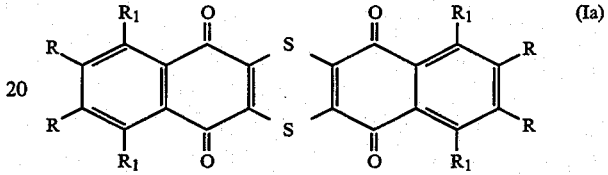

with equimolar amounts of $TiCl_4$ and $[(CH_3)_3SiN]_2C$ in an inert solvent under an inert atmosphere for 10 to 30 hours.

13. A process according to claim 12, wherein the inert atmosphere is an argon atmosphere.

* * * * *